(12) United States Patent  
Ackley et al.

(10) Patent No.: US 9,164,017 B2  
(45) Date of Patent: Oct. 20, 2015

(54) IDENTIFICATION OF PLASTIC MATERIAL COMPOSITION

(71) Applicant: International Business Machines Corporation, Armonk, NY (US)

(72) Inventors: Sean M. Ackley, Raleigh, NC (US); Camillo Sassano, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 98 days.

(21) Appl. No.: 13/766,989

(22) Filed: Feb. 14, 2013

(65) Prior Publication Data

US 2013/0341249 A1 Dec. 26, 2013

Related U.S. Application Data

(62) Division of application No. 13/532,082, filed on Jun. 25, 2012, now Pat. No. 9,000,318.

(51) Int. Cl.  
*B07C 5/00* (2006.01)  
*G01N 3/06* (2006.01)  
*G01N 21/25* (2006.01)

(52) U.S. Cl.  
CPC .............. *G01N 3/068* (2013.01); *G01N 21/251* (2013.01)

(58) Field of Classification Search  
CPC ........ B07B 13/003; B03B 9/00; B07C 5/362; B07C 5/36; B07C 5/344; B07C 5/366; B07C 5/342; B07C 1/00; B07C 2501/0054; B07C 2501/0072; G01N 27/80

USPC ................ 209/2, 552, 567, 571, 576, 3, 699; 241/24.12, 24.18

See application file for complete search history.

(56) References Cited

U.S. PATENT DOCUMENTS

| | | | |
|---|---|---|---|
| 2,707,555 A * | 5/1955 | Gaudin ...................... 376/157 |
| 3,356,211 A * | 12/1967 | Mathews ...................... 209/3.1 |
| 5,255,859 A | 10/1993 | Peacock et al. |
| 5,703,229 A | 12/1997 | Krutak et al. |
| 6,845,869 B1 | 1/2005 | Graf von Deym et al. |
| 7,081,217 B2 | 7/2006 | Treleaven |
| 7,172,143 B2 | 2/2007 | Vandeputte |
| 7,799,835 B2 * | 9/2010 | Smith et al. ...................... 521/40 |
| 7,802,685 B2 | 9/2010 | Allen et al. |
| 2009/0285258 A1 | 11/2009 | Kinami |
| 2010/0140476 A1 * | 6/2010 | Werner et al. ............ 250/339.07 |

FOREIGN PATENT DOCUMENTS

JP 2009300411 A 12/2009

* cited by examiner

*Primary Examiner* — Thomas Morrison  
(74) *Attorney, Agent, or Firm* — Lieberman & Brandsdorfer, LLC (57) ABSTRACT

Identification of a material composition. The material composition is configured with a color additive that is embedded or otherwise not visible. The color additive identifies the specific material composition. A discrete section or sub-section of the material is deformed such that the embedded color additive is made visible in the optical spectrum, after which the discrete section or sub-section may be sorted for recycling.

12 Claims, 5 Drawing Sheets

IDENTIFICATION OF PLASTIC MATERIAL COMPOSITION

CROSS REFERENCE TO RELATED APPLICATION(S)

This application is a divisional patent application claiming the benefit of the filing date of U.S. patent application Ser. No. 13/532,082 filed on Jun. 25, 2012, and titled "Identification of Plastic Material Composition" now pending, which is hereby incorporated by reference.

BACKGROUND

1. Technical Field

The present invention relates to a method and system for identifying the composition of a material. More specifically, the invention relates to a method and system that bases the identification on transformation of the material between a first state and a second state.

2. Description of the Prior Art

The art of recycling material addresses converting used materials into new products to prevent waste and pollution associated with product disposal. One aspect of recycling includes identification of the material to be recycled, as different materials may be subject to different recycling processes. Recyclable materials include items such as glass, paper, metal, plastic, textile, etc, each of which may be subject to different processes of recycling. Accordingly, separation of materials based on the material composition is an aspect of the recycling process.

A current state of the art engraves a material code into the product material. The engraved code identifies the material composition with an associated number. This code is employed in the material separation process, and provides efficiency in that material compositions can be identified and sorted based on the engraved number. Problems in product recycling arise when the material code is not attached to or otherwise embedded in the product or product material. Post-consumer materials are often intentionally or unintentionally broken or disassembled before they are sorted. Many fragmented pieces of material are left absent the material code, causing the piece's compositions to be unidentifiable and thus unrecyclable.

SUMMARY OF THE INVENTION

This invention comprises a method for identifying a composition of a material.

In one aspect, a method is provided to identify the composition of a first material. The method includes application of a force to a body in a first state. The body includes a first material and a second material in communication with the first material, with the second material having a different property than the first material. In the first state, and prior to application of force to the body, the second material is not visible within the optical spectrum. Following application of force, the body is placed in a second state, such that the second material is visible in the optical spectrum. The second state is different from the first state. The method further includes identifying the composition of the first material based on a characteristic of the visible second material.

In another aspect, a method is provided to identify the composition of a material. The method includes deforming a body beyond an associated deformation range, with the body including two materials with two different properties. Beyond the associated deformation range the second material becomes visible in the optical spectrum. An optical wavelength is observed as indicated by the second material. The observed optical wavelength is used to identify a composition of the body.

BRIEF DESCRIPTION OF THE DRAWINGS

The drawings referenced herein form a part of the specification. Features shown in the drawings are meant as illustrative of only some embodiments of the invention, and not of all embodiments of the invention unless otherwise explicitly indicated. Implications to the contrary are otherwise not to be made.

DETAILED DESCRIPTION

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

Reference throughout this specification to "a select embodiment," "one embodiment," or "an embodiment" means that a particular feature, structure, or characteristic described in connection with the embodiment is included in at least one embodiment of the present invention. Thus, appearances of the phrases "a select embodiment," "in one embodiment," or "in an embodiment" in various places throughout this specification are not necessarily referring to the same embodiment.

Furthermore, the described features, structures, or characteristics may be combined in any suitable manner in one or more embodiments. In the following description, numerous specific details are provided, such as examples of modules, managers, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of devices, systems, and processes that are consistent with the invention as claimed herein.

In the following description of the embodiments, reference is made to the accompanying drawings that form a part hereof, and which shows by way of illustration the specific embodiment in which the invention may be practiced. It is to be understood that other embodiments may be utilized because structural changes may be made without departing form the scope of the present invention.

Figure 1:
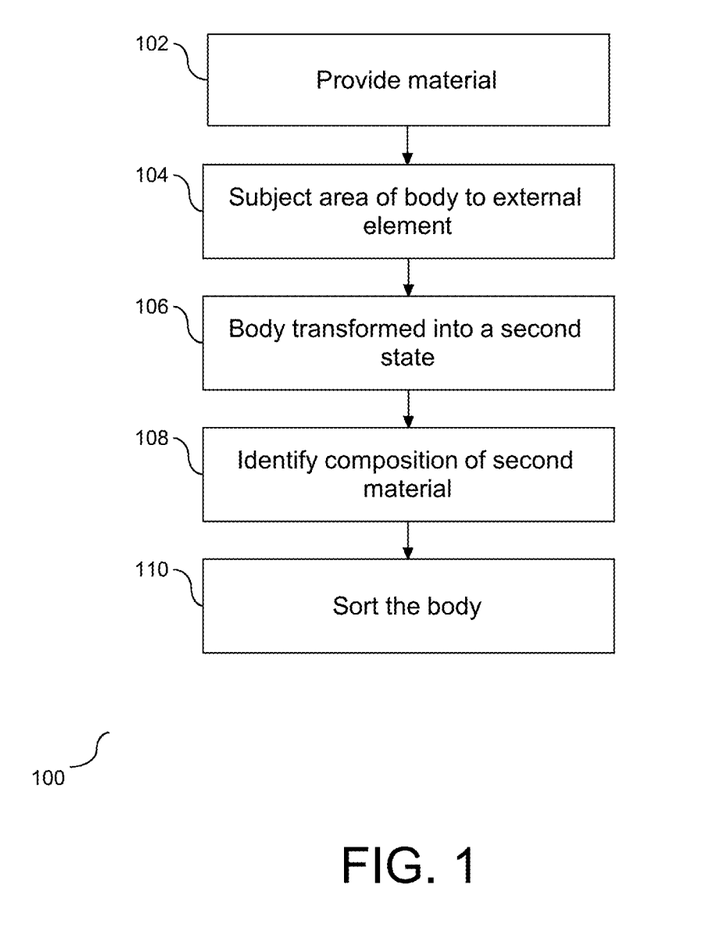
FIG. 1 depicts a flow chart illustrating a process for material composition identification.

Products comprised of plastic material are commonly recycled following disposal of the product. FIG. 1 is a flow chart (100) illustrating a process for optically identifying a composition of a body based upon a transformation of material associated with the body. A material composition is provided in the form of a body (102). Specifically, the composition includes at least two materials, a first material and a second material. At such time as the body is provided at step (102), only one of the first and second materials is visible on the optical spectrum. As such, identification of the body based upon a visible characteristic of the body is limited to material that is visible in the optical spectrum. Different materials may be embedded with different second materials, with each second material having a different color that is visible in the optical spectrum. Each embedded color is associated with a different material of the body. For example, blue may be associated with a first category of plastic material that is recycled through a first recycling process, red may be associated with a second category of plastic material that is recycled through a second recycling process, etc. Accordingly, the color of the embedded material in the optical spectrum identifies the composition of the body, and also identifies a specific recycling process for the body.

With only one of the materials visible, as defined above, the body is considered to exist in a first state. At such time as the second material is visible in the optical spectrum, the body is considered to exist in a second state. Accordingly, prior to a transformation of the body from the first state, only one of the materials is visible in the optical spectrum with identification of the body limited to the visible material.

In the first state, the composition of the visible material is identifiable. With respect to the art of recycling materials, the body may be disassembled, and as a result the identification of the composition of the body material may become challenging if not impossible. An area of the body is subject to an external element that transforms the body from the first state to a second state (104). In one embodiment, the transformation takes place following application of a force to the body. Similarly, in one embodiment, the transformation is a result of a subsection of the body being subject to a deformation. Regardless of the specific application at step (104), the body changes from a first state to a second state (106). The body is comprised of at least two materials, including a first material and a second material. As noted above, in the first state the second material is not visible in the optical spectrum. In the second state, the second material is visible in the optical spectrum. Accordingly, the transformation of the body from the first state to the second state is reflected in visibility of the second material in the optical spectrum.

Following transformation of the body between states, the composition of the second material is identified (108). The second material is visible in the optical spectrum once the body is in the second state. Identification may take place with the naked eye or with a tool. In one embodiment, the second material is comprised of a pigment associated with a color additive, wherein this pigment is different from a visible property associated with the first material. For example, if the first material is black, the second material may be a pigment such as white, blue, green, red, orange, yellow, etc., or any color that is visible in the optical spectrum or otherwise reflects an optical wavelength. Accordingly, the body is configured such that the second material becomes visible in the optical spectrum by reflecting an optical wavelength when the body is in the second state.

By embedding the second material in the body and limiting exposure of the second material to the second state of the body, the composition of the body may be identified. More specifically, the body may be a second body that has been separated or otherwise severed from a primary body. By embedding the second material and making the second material visible, the composition of the second body may be identified at a later point in time. For example, in the art of recycling of materials, an original body may be fragmented into a plurality of secondary bodies prior to sorting, and as such the material of the secondary bodies may not be readily identifiable. The secondary material has a secondary property, which in one embodiment may identify the composition of the second body. Based upon the composition identification, the first or second body may be sorted (110). More specifically, sorting of materials commonly takes place in the art of recycling. Each identified second body may be sorted for proper recycling, thereby mitigating waste and improper disposal of the second body.

Figure 2:
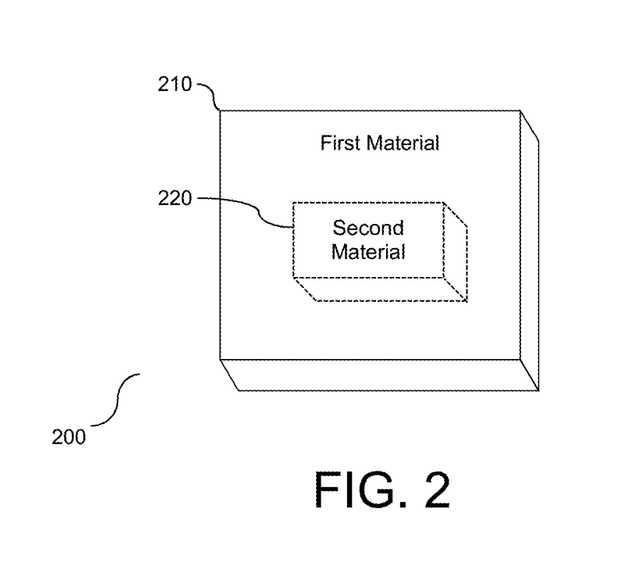
FIG. 2 depicts a block diagram of the material in a first state.

FIG. 2 is a block diagram (200) of a body in a first state, i.e. prior to deformation. As shown, the body (200) is comprised of two materials, including a first material (210) and a second material (220). The first state of the body is prior to any application of force, or another form of deformation of the body. The first material (210) is the only material of the body (200) that is visible in the optical spectrum in the first state. The second material (220) is embedded or otherwise surrounded by the first material (210). Accordingly, the second material (220) is not visible in the optical spectrum in the first state.

Figure 3:
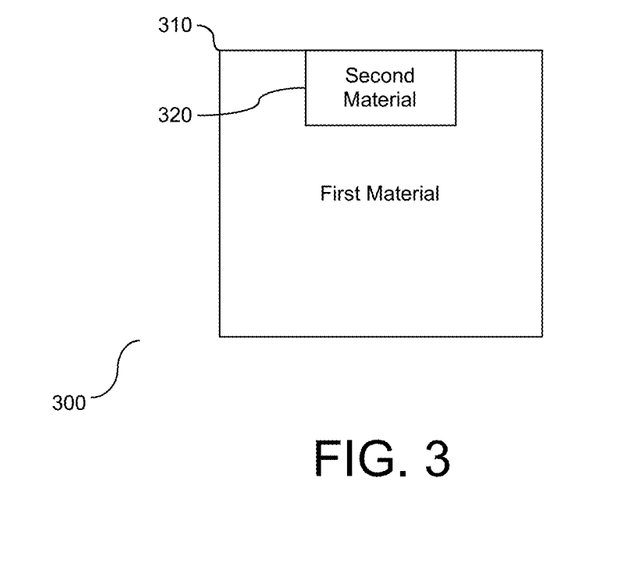
FIG. 3 depicts a block diagram of the material in a second state.

FIG. 3 is a block diagram (300) of the body in a second state. The body is in a second state subsequent to application causing a deformation to the body exceeding a corresponding deformation range. The deformation range is defined to be exceeded when the second material (320) is visible in the optical spectrum. The second material (320) being visible, enables the composition of the body to be identified, specifically the composition of the first material (310). Deformation of the body takes the body from the first state to the second state, and can take place in different forms. For example, deformation may be the application of force to the body, a shearing of an external layer of the visible material until the embedded material is visible, etc. In one embodiment, the first material is comprised of plastic material that is subject to a permanent deformation, also known as a uniform plastic deformation. Once subject to the deformation beyond its yield strength point, the second material in the form of an embedded elastomer becomes visible and remains visible after the stressor ceases application to the body. Accordingly, deformation of the body is not limited to a specific embodiment, as it may encompass any embodiment that enables the layered or embedded second material to be visible in the optical spectrum.

Figure 4:
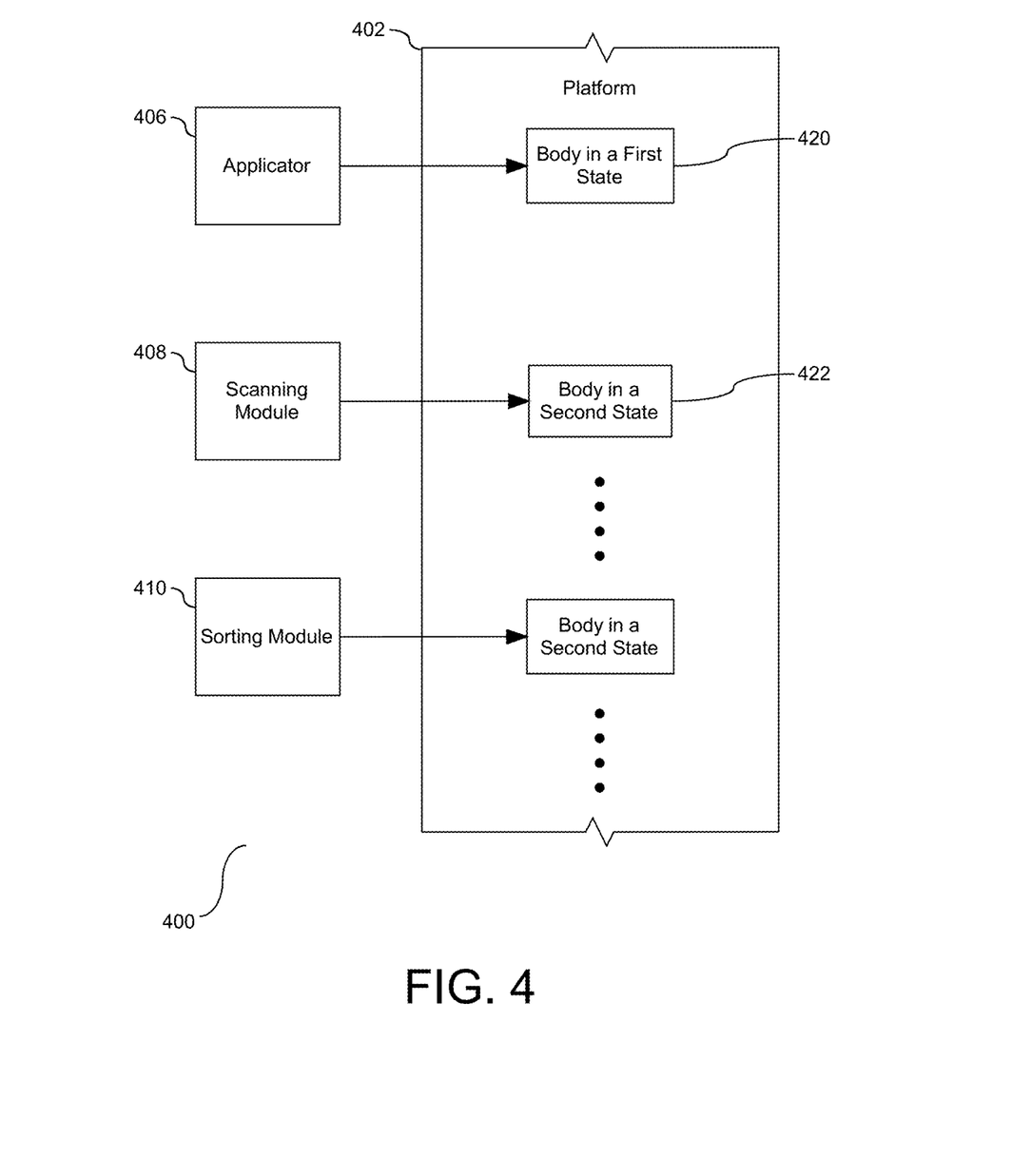
FIG. 4 depicts a block diagram illustrating tools embedded in a system to support material composition identification.

The identification of the body material can take place in different formats. For example, the identification may be manually enabled, whereby a person may visually identify the composition of the body material. In another embodiment, the deformation and/or identification may be automated or semi-automated to mitigate human error. FIG. 4 is a block diagram (400) for a system employed to deform and identify the composition of the body. The system provides a platform (402) for carrying a body in a first state, and in one embodiment a second state (420). Details of the first state and second state are shown and explained above with reference to FIGS. 2 and 3. An applicator (406) applies an external force to the body in a first state (420) causing the body to subsequently transform into a second state (422). Details of the second state are shown and explained above with referenced to FIG. 3. This applied force can be in many forms including but not limited to, a sheering of the body past a target layer, a puncturing of the body, application of stress or strain to any portion of the body, etc. Regardless of the manner of deformation, the deformation of the body is completed when the body has attained the second state. Specifically, the body is considered transformed into the second state (422) when the second material of the body (320) is visible in the optical spectrum.

A scanning module (408) observes the body, and determines if the body is in the first state or the second state. When the body is in the second state (422), the originally embedded material is visible within the optical spectrum, and the scanning module (408) identifies a characteristic of the second material. In one embodiment, the revealed characteristic of the second material is a distinguishable color. The characteristic of the second material corresponds with a particular material composition. Specifically, the composition of the body is defined upon identification of the second material. For example, if in one embodiment the second material being the color blue was chosen to identify ABS plastic (plastic composed of varying proportions of acrylonitrile, butadiene, and styrene), then the scanning module observing the color blue would identify the body to contain ABS plastic. It is the purpose of the scanning module to observe a characteristic of the second material (320) of the body in a second state (422), and identify a composition of the body using the observed characteristic.

A sorting module (410) is provided in communication with the platform (402). The sorting module (410) sorts the body based on an identified composition of the material. This sorting process involves compiling materials of like composition. In one embodiment of the invention, the platform (402) carries the body for processing from the applicator (406) to the scanning module (408), and then from the scanning module (408) to the sorting module (410). The sorting of the material allows for recycling of the material with like compositions. Materials that would otherwise be unidentifiable can often not be recycled and are wasted.

Figure 5:
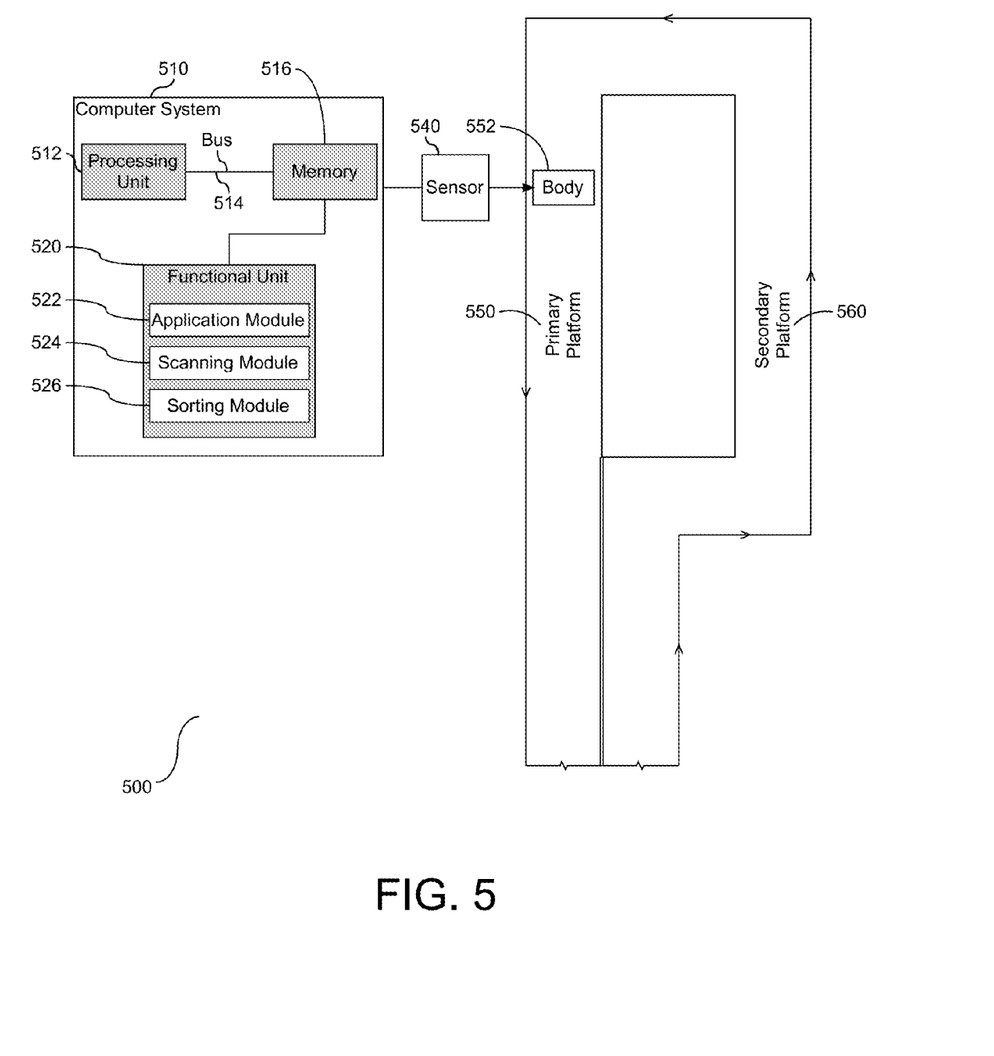
FIG. 5 is a block diagram illustrating tools embedded in a system to support material identification.

As demonstrated in FIG. 4, a plurality of modules may be employed to deform a body, visually assess a body composition subsequent to the deformation, and based upon the visual assessment sort the material. FIG. 5 is a block diagram (500) illustrating tools embedded in a system to support automated assessment of the material composition of a body. For illustrative purposes, a computer system (510) is provided in communication with a primary platform (550). The computer system (510) is provided with a processing unit (512) in communication with memory (516) across a bus (514). The computer system (510) is shown in communication with a sensor (540). In one embodiment, the sensor (540) may be a part of or in communication with the primary platform (550). A functional unit (520) is provided in communication with memory (516). The functional unit (520) supports management of material identification.

The sensor (540) functions in communication with the primary platform (550) to read detect the presence of the body (552) on the primary platform (550). In one embodiment, each body of material (552) is a discrete element. The functional unit (520) is shown herein with several tools for management of identification of the material of the body (552). Specifically, the tools include, but are not limited to, an application module (522), a scanning module (524), and a sorting module (526). The application module (522) is in communication with the sensor (540), and receives position data of the body (552) with respect to the primary platform (550). Based upon the position data, the application module deforms the body of material (552) to transform the body (552) from a first state to a second state. The scanning module (524) scans the body of material (552) to determine if the material (552) is in the second state. More specifically, the scanning module (524) visually assesses the state of the body of material (552). In one embodiment, the scanning module (524) communicates with the sorting module (526) to sort the body of material only when the scanning module has visually assessed the body of material to be in the second state, e.g. when the second material is visible in the optical spectrum. Accordingly, the application module (522) and scanning module (524) function to transform the state of a body of material from a first state to a second state, with the sorting module (526) functioning to sort the body of material in response to the body transformation.

As explained herein, the scanning module (524) functions to identify presence of the body of material (552) on the primary platform (550), and also to assess the transformation of the body between states. In one embodiment, a secondary platform (560) is provided in communication with the primary platform (550), with the secondary platform (560) provided to accept a transfer of material bodies that have not attained a second state from the application module (522). Similarly, in one embodiment, the transferred bodies may be subject to a repeat exposure to the scanning and application modules (522) and (524), respectively.

The sensor (540) is provided in communication with the application and scanning modules (522) and (524), respectively, of the functional unit (520). More specifically, the sensor (540) detects presence of the material on the primary platform (550), and in one embodiment, the secondary platform (560). The detected presence of the material initiates deformation of the detected material by the application module (522), following by a scan of the material by the scanning module (524) to detect characteristics of the material in the second state. The detected second state of the material supports sorting of the material. The sensor (540) effectively communicates the threshold attainment of the material by communication with the sorting module (526), or the secondary platform (560). Accordingly, as shown herein, tools in the form of modules are provided to assess presence of a material body, and dynamically transform the body to a second state to enable proper sorting of the material body responsive to identification of the material composition of the body.

As identified above, the application module (522), scanning module (524), and sorting module (526), hereinafter referred to as tools, function as elements to dynamically assess the material composition of a body. The tools (522)-(526) are shown residing in memory (516) local to the computing device (510). However, the tools (522)-(526) may reside as hardware tools external to the memory (516), or they may be implemented as a combination of hardware and software. Similarly, in one embodiment, the tools (522)-(526) may be combined into a single functional item that incorporates the functionality of the separate items. As shown herein, each of the tools (522)-(526) are shown local to the computing device (510). However, in one embodiment they may be collectively or individually distributed across a network or multiple machines and function as a unit to dynamically assess and manage material identification. Accordingly, the tools may be implemented as software tools, hardware tools, or a combination of software and hardware tools.

As will be appreciated by one skilled in the art, aspects of the present invention may be embodied as a system, method or computer program product. Accordingly, aspects of the present invention may take the form of an entirely hardware based embodiment, an entirely software based embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 6:
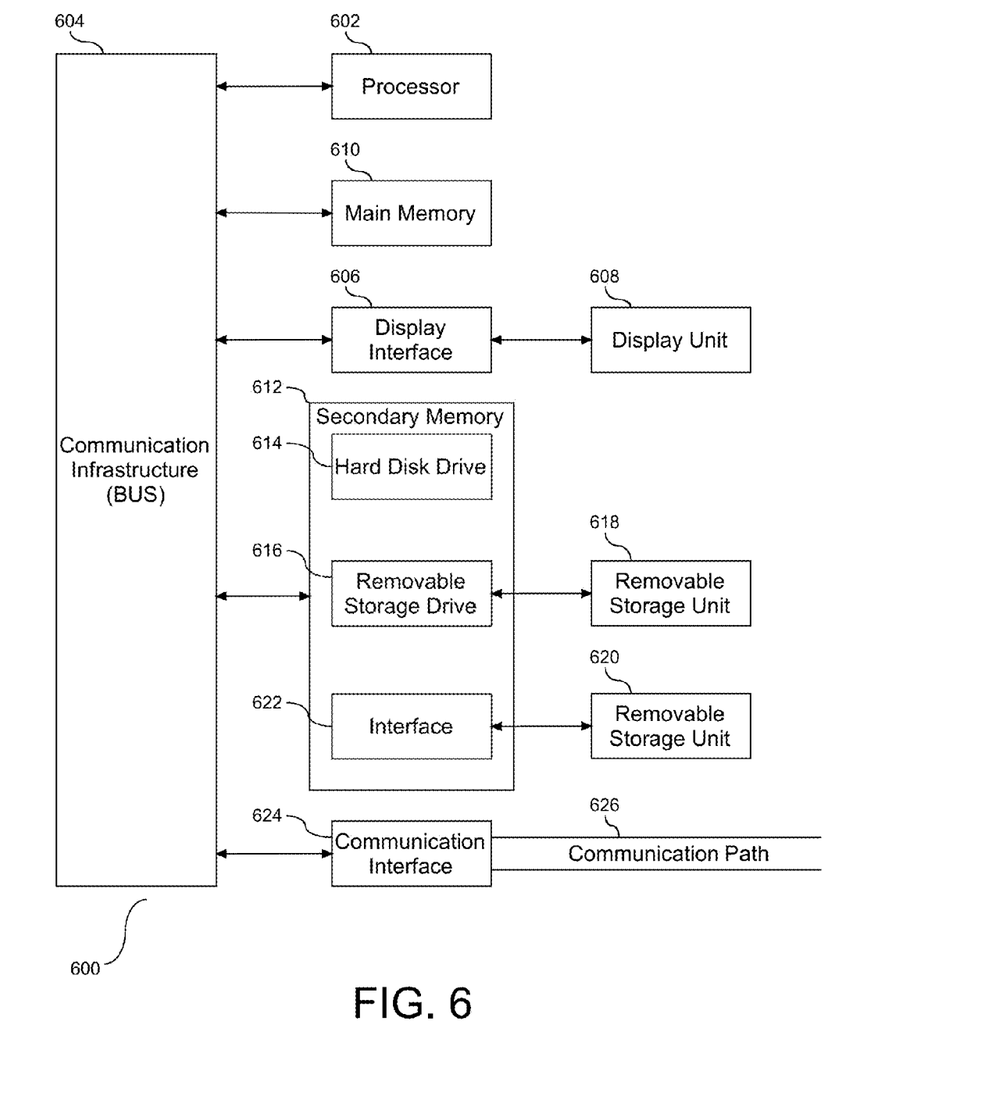
FIG. 6 depicts a block diagram showing a system for implementing an embodiment of the present invention.

Referring now to the block diagram of FIG. 6, additional details are now described with respect to implementing an embodiment of the present invention. The computer system includes one or more processors, such as a processor (602). The processor (602) is connected to a communication infrastructure (604) (e.g., a communications bus, cross-over bar, or network).

The computer system can include a display interface (606) that forwards graphics, text, and other data from the communication infrastructure (604) (or from a frame buffer not shown) for display on a display unit (608). The computer system also includes a main memory (610), preferably random access memory (RAM), and may also include a secondary memory (612). The secondary memory (612) may include, for example, a hard disk drive (614) and/or a removable storage drive (616), representing, for example, a floppy disk drive, a magnetic tape drive, or an optical disk drive. The removable storage drive (616) reads from and/or writes to a removable storage unit (618) in a manner well known to those having ordinary skill in the art. Removable storage unit (618) represents, for example, a floppy disk, a compact disc, a magnetic tape, or an optical disk, etc., which is read by and written to by removable storage drive (616). As will be appreciated, the removable storage unit (618) includes a computer readable medium having stored therein computer software and/or data.

In alternative embodiments, the secondary memory (612) may include other similar means for allowing computer programs or other instructions to be loaded into the computer system. Such means may include, for example, a removable storage unit (620) and an interface (622). Examples of such means may include a program package and package interface (such as that found in video game devices), a removable memory chip (such as an EPROM, or PROM) and associated socket, and other removable storage units (620) and interfaces (622) which allow software and data to be transferred from the removable storage unit (620) to the computer system.

The computer system may also include a communications interface (624). Communications interface (624) allows software and data to be transferred between the computer system and external devices. Examples of communications interface (624) may include a modem, a network interface (such as an Ethernet card), a communications port, or a PCMCIA slot and card, etc. Software and data transferred via communications interface (624) are in the form of signals which may be, for example, electronic, electromagnetic, optical, or other signals capable of being received by communications interface (624). These signals are provided to communications interface (624) via a communications path (i.e., channel) (626). This communications path (626) carries signals and may be implemented using wire or cable, fiber optics, a phone line, a cellular phone link, a radio frequency (RF) link, and/or other communication channels.

In this document, the terms "computer program medium," "computer usable medium," and "computer readable medium" are used to generally refer to media such as main memory (610) and secondary memory (612), removable storage drive (616), and a hard disk installed in hard disk drive (614).

Computer programs (also called computer control logic) are stored in main memory (610) and/or secondary memory (612). Computer programs may also be received via a communication interface (624). Such computer programs, when run, enable the computer system to perform the features of the present invention as discussed herein. In particular, the computer programs, when run, enable the processor (602) to perform the features of the computer system. Accordingly, such computer programs represent controllers of the computer system.

The flowchart(s) and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed.

Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Alternative Embodiment

It will be appreciated that, although specific embodiments of the invention have been described herein for purposes of illustration, various modifications may be made without departing from the spirit and scope of the invention. Accordingly, the scope of protection of this invention is limited only by the following claims and their equivalents.

We claim:

1. A method comprising:
applying a force to an area of a body, the body comprising a first material and a second material, the first material having a first property and the second material in communication with the first material and having a second property, the second property different from the first property, and the second property of the second material being non-visible in an optical spectrum in a first state of the body;
the force transforming the body to a second state, different from the first state, including making visible a characteristic of the second material reflecting at least one optical wavelength; and
identifying a composition of the first material based on the visible characteristic of the second material in the second state.

2. The method of claim 1, further comprising sorting the first material based on the identified composition.

3. The method of claim 1, wherein the first material is plastic.

4. The method of claim 1, wherein the second material is a color additive.

5. The method of claim 4, wherein the visible characteristic of the second material in the second state includes a pigment associated with the color additive and different from a visible property associated with the first material.

6. The method of claim 5, wherein the pigment is associated with an identifiable material.

7. The method of claim 1, further comprising identifying the visible characteristic of the second material with an optical scanner.

8. The method of claim 1, wherein application of the force to the body results in deformation of the body beyond an associated elastic deformation range.

9. The method of claim 1, wherein the communication between the second material and the first material includes the second material layered underneath an exposed surface of the first material.

10. The method of claim 1, wherein the communication between the second material and the first material includes the second material embedded in the first material.

11. A method comprising:
deforming a body beyond an associated deformation range, the body comprised of a first material having a first property and a second material having a second property, the deformation making visible the second material in an optical spectrum;

observing an optical wavelength indicated by a color indicator in response to deformation of the body; and identifying a composition of the body based on the observed optical wavelength of the second material.

12. The method of claim 11, further comprising sorting the body based on the identified composition.

* * * * *